US006539774B1

(12) United States Patent
Zinck et al.

(10) Patent No.: US 6,539,774 B1
(45) Date of Patent: Apr. 1, 2003

(54) THIN FILM METAL HYDRIDE HYDROGEN SENSOR

(75) Inventors: Jennifer J. Zinck, Calabasas, CA (US); Deborah J. Kirby, Calabasas Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 09/710,604

(22) Filed: Nov. 10, 2000

(51) Int. Cl.[7] .......................... G01N 19/10; G01N 7/00; G01N 33/00

(52) U.S. Cl. .................. 73/23.2; 73/31.05; 436/144

(58) Field of Search .................. 73/23.2, 31.05; 436/144; 123/3

(56) References Cited

U.S. PATENT DOCUMENTS

| | | | |
|---|---|---|---|
| 3,732,076 A | 5/1973 | Toy et al. | 436/144 |
| 4,921,346 A | 5/1990 | Tokumoto | 356/72 |
| 5,305,714 A | 4/1994 | Sekiguchi et al. | 123/3 |
| 6,006,582 A | 12/1999 | Bhandari et al. | 73/23.2 |
| 6,029,500 A | 2/2000 | Tom | 73/31.05 |
| 6,265,222 B1 | 7/2001 | DiMeo, Jr. et al. | 436/144 |
| 2002/0226794 | 3/2002 | Shahinpoor et al. | 60/508 |

FOREIGN PATENT DOCUMENTS

WO 94/28372 12/1994

OTHER PUBLICATIONS

Patent Abstracts of Japan, vol. 014, No. 422 (Sep. 12, 1990).
Adachi, Gin–Ya, et al., "The effect of hydrogen absorption on the electrical resistivity of $LaNi_5$ film", *Journal of the Less–Common Metals*, vol. 81, pp. 345–348, (1981).
Anisimkin, V.I., et al., "Advanced Pd–Based Saw Hydrogen Sensors: Theoretical Approach", Institute of Radioengineering and Electronics, Russian Academy of Sciences, Russia, pp. 195–198.
Anisimkin, V.I., et al., "Advanced Pd–Based Saw Hydrogen Sensors: Experimental Approach", Institute of Radioengineering and Electronics, Russian Academy of Sciences, Russia, pp. 199–203.
Baxter, Larry K., "Capacitive Sensors: Design and Applications", *The Institute of Electrical and Electronics Engineers, Inc.*, New York, pp. 48–60.
"Functional sensor materials/Table 2", *Advanced Polymer Composites*, p. 230 (abstract).
Gerard, Norbert, et al., "Hydride Formation and Decomposition Kinetics", *Topics of Applied Physics*, vol. 67, pp. 165–195.
Lee, Sang Mae, et al., "Hydrogen Sensor Based on Palladium–Attached Fiber Bragg Grating", *Journal of the Optical Society of Korea*, vol. 3, No. 2, pp. 69–73, (Sep. 1999).
"Low–Cost Gas Sensors for Fuel Cell–Powered Vehicles", "Research Results", Illinois Institute of Technology, http://www.ipd.anl.gov/carat/iit_results.htm, 1 page.

(List continued on next page.)

Primary Examiner—Hezron Williams
Assistant Examiner—Jay L Politzer
(74) Attorney, Agent, or Firm—Ladas & Parry (57) ABSTRACT

A sensor for determining the presence of hydrogen and for measuring the amount of hydrogen present in the vicinity of the sensor. The sensor comprises a metal hydride hydrogen-absorbent material $AB_5$ which selectively absorbs hydrogen and expands upon such absorption. This expansion depends on the amount of hydrogen absorbed and the expansion is detected and measured either by measurement of a change in capacitance of the sensor or by the change in tunnel current flowing through the sensor. A method for determining the presence of hydrogen and for measuring the amount of hydrogen present using the metal hydride hydrogen-absorbent material $AB_5$-based sensor.

37 Claims, 4 Drawing Sheets

OTHER PUBLICATIONS

Nave, Stanley E., "FY 97 Report on Hydrogen Sensors for Enhanced Surveillance Program Project LL–ESP96–13 (U)", WSRC–RP–97–00904 Rev 0, pp. 1–14, (Sep. 30, 1997).

Sakai, T., et al., "Thin Film Preparation of Hydrogen Storage Alloys and Their Characteristics as Metal Hydride Electrodes", *Journal of Electrochemistry Society,* vol. 138, No. 4, pp. 908–915, (Apr. 1991).

Sandrock, Ph.D., Gary, "State of the Art Review of Hydrogen storage in Reversible Metal Hydrides for Military Fuel Cell Applications", 19970801 035, SunaTech, Inc., New Jersey, pp. 29–43, (Jul. 24, 1997).

Siegmann, et al., "Self–Restoring of the Active Surface in the Hydrogen Sponge $LaNi_5$", *Physical Review Letters,* vol. 40, No. 14, pp. 972–974, (Apr. 3, 1978).

THIN FILM METAL HYDRIDE HYDROGEN SENSOR

BACKGROUND OF THE INVENTION

1. Field of the Invention

This invention relates generally to a gas sensor for detecting the presence of hydrogen in gas streams or in the environment, and for measuring the amount of such hydrogen. More particularly, in order to accomplish such detection the invention utilizes thin film technology, as well as a methodology for sensing the presence of hydrogen gas in such gas streams or environments.

2. Description of the Related Art

Hydrogen is a flammable and explosive gas with a wide variety of industrial and scientific uses. Well-known industrial uses of hydrogen include the production of basic staple products of chemical industry such as ammonia and fertilizers derived therefrom, basic alcohols, hydrogen chloride, reduction of ores for manufacturing of metals, refinery of oil for manufacturing of petroleum, hydrogenation of vegetable oils for margarine and related industries, and many other uses.

Hydrogen is also widely used for space flight applications, for instance as a component of hydrogen-oxygen blends used in vehicular propulsion systems.

Hydrogen is also used in a variety of metal forming and microelectronic processing steps which are often of extreme importance in device fabrication and metal interconnect processing of multi-level devices.

There has been also an increasing emphasis on the use of fuel cells, which require hydrogen as a fuel in various stationary and mobile applications, for instance, in fuel cells of automobiles.

It is axiomatic that handling hydrogen requires utilization of robust safety devices as it is a highly flammable gas at a concentration in air as low as 4% by volume. The ability to detect stray emissions of hydrogen is, therefore, mandatory, and is an important feature of any process or device where hydrogen is used.

In these and other applications, hydrogen sensors are employed to monitor the environment around which hydrogen is utilized, to ensure the efficiency, safety and operational integrity of the system. For such purposes, a number of hydrogen sensors and complex detection methods have been developed and are in common use.

A variety of these commercially available hydrogen sensors are based on measuring an electrical characteristic across a sensor element and at least four major categories of sensors and associated methods can be identified.

One type of hydrogen sensor is the "catalytic combustible" or "hot wire" sensor (CC sensor) mentioned in the U.S. Pat. No. 6,006,582 to Bhandari, et. al. The CC sensor comprises two specially arranged beads of a catalytic metal or alloy, such as platinum-iridium wire heated to 600–800° C. One bead is coated with a reactive catalyst. In the presence of a flammable gas, the heat of oxidation raises the temperature of the bead and alters the electrical resistance characteristics of the measuring circuit. This resistance change is related to the concentration of all flammable gases, including hydrogen, in the vicinity of the sensor.

The CC sensor has serious drawbacks. In oxygen deficient environments or above an upper explosive limit, the oxidation process is quenched causing difficulties in measuring. In addition, since the CC sensor is based upon oxidation, virtually any and all hydrocarbons have the same response as hydrogen, making it difficult to detect hydrogen in the environments which also contain hydrocarbons. Finally, the CC sensor element is easily contaminated by halogenated hydrocarbons and is susceptible to poisoning by silicones, lead and phosphorous.

Another commonly used hydrogen sensor is a non-porous metal oxide (MO) sensor. The MO sensor element comprises a non-porous metal oxide (such as zirconium dioxide or tin dioxide) sandwiched between two porous metal electrodes. Such electrodes are typically made of platinum. One electrode is exposed to the reference gas, usually, air, and the other—to test gas being detected.

Mobile ions diffuse to both surfaces of the oxide where they may be eliminated by reaction with adsorbed species. In the absence of gas species which can be oxidized (such as, for instance, carbon monoxide or hydrogen), the electrochemical potential of the sensor may be determined by the Nernst equation and is proportional to the partial pressure of oxygen in the test gas only. In order to achieve sensitivity to hydrogen with this device, the platinum electrode is co-deposited with gold. Since gold is a substantially less efficient donor of electrons than platinum, oxidation rates are reduced, equilibrium conditions are not achieved and the sensor response is sensitive to the composition of the test gas. The electrochemical potential which develops becomes non-Nernstian, and is a complicated function of the kinetics and mass transfer associated with all species reacting at the electrode.

Just like the CC sensor, the MO sensor has serious disadvantages. The sensor is not hydrogen-specific and all oxidizable gases in the test gas contribute to the sensor signal. The response is relatively slow and it can take up to 20 seconds to reach 50% of maximum signal when exposed to 1% hydrogen in air at flows below 200 standard cubic centimeters per minute (sccm); the recovery time is even slower taking up to 5 minutes to reach 50% of maximum signal when exposed to less than 200 sccm of air. Finally, in order to achieve even these orders of response time, the device must be operated at temperatures above 350° C. Operating at such temperatures, just as in case of the MOS sensors, subsequently discussed, is potentially unsafe and may cause ignition and/or explosion.

Yet another type of sensor is the metal oxide-semiconductor (MOS) sensor which is also known and is mentioned, for instance, in the U.S. Pat. No. 6,006,582 to Bhandari, et. al. The MOS sensor element comprises an oxide, typically of iron, zinc, or tin, or a mixture thereof, and is heated to a temperature of between about 150° C. and about 350° C. Bhandari et. al. reported that oxygen absorbs on the surface of the sensor element to create an equilibrium concentration of oxide ions in the surface layers.

The original resistance of the MOS sensor is first measured. When certain compounds, such as, for instance, CO, or hydrocarbons come in contact with the sensor, they are adsorbed on the surface of the MOS element. This absorption shifts the oxygen equilibrium, causing a detectable increase in conductivity of the MOS material.

MOS hydrogen sensors have a number of operational deficiencies and are, therefore, unsatisfactory in many respects. They require frequent calibration and their response times are too long (up to 3–5 minutes). Bhandari et. al. noted that the MOS sensors are unsafe and can cause ignition and explosion, and are susceptible to being poisoned with halogenated vapors. Like the CC and the MO sensors discussed above, they are not hydrogen specific. All volatile organic compounds as well as gases containing hydrogen will react with the sensor materials in the sensing elements of these detectors, thereby providing false readings.

Still yet another sensor is the catalytic gate (CG) sensor, the simplest embodiment of which is a MOS structure, where the metal is usually platinum or palladium deposited on an insulator, such as silicon dioxide. Hydrogen dissociates on platinum or palladium and subsequently diffuses into the bulk of the metal. Hydrogen atoms which arrive at the metal-insulator interface, form a dipole layer, polarizing the interface and consequently changing its electrical characteristics. The CG sensor also has serious drawbacks, particularly slow response time when the surface is contaminated. The surface of platinum or palladium is very much susceptible to contamination and poisoning.

There exists no known prior art teaching a hydrogen-specific sensor, which is immune to the interference from other gases, which quickly responds and which is not susceptible to poisoning. Yet, as discussed above, such sensor is highly desirable and the need for such sensor, which is also low cost, lightweight and of a miniature size, is acute.

The present invention discloses such sensor. It therefore is an object of the present invention to provide an improved hydrogen sensor and hydrogen sensing methodology overcoming the aforementioned deficiencies of the previously known hydrogen detectors.

SUMMARY OF THE INVENTION

The present invention is directed to a hydrogen sensor based upon an $AB_5$-based class of metal hydride materials described below. Materials of this type are capable of reversibly adsorbing hydrogen, first as a so-called $\alpha$-hydride solid solution, and then as an ordered $\beta$-hydride phase. The reactions of hydrogenization or dehydrohenization are very fast and in most applications the speed of these reactions is limited only by heat transfer between particles. Diffusion of hydrogen is controlled and proportional to the square root of pressure of hydrogen, according to Sievert's law. See, H. Gerard and S. Oho, Hydrogen in Intermetallic Compounds II, Chapter 4, Springer-Verlag, 1992. Thus, the detection of hydrogen is very quick.

This invention takes advantage of a fact that $AB_5$-based metal hydride materials are characterized by large volume expansion when they are absorbing hydrogen. For example, $LaNi_5$ exhibits about 30% lattice expansion by volume (about 8.4% along the "a" axis and about 8.1% along the "c" axis) upon having absorbed the maximum amount of about 1.5% of hydrogen by weight. Crystalline thin films of $LaNi_5$ have been successfully deposited on glass substrates and, upon absorption of hydrogen, exhibited lattice expansion only in a direction perpendicular to the substrate. See, for example, T. Sakai, et. al., J. Electrochem. Soc., 138, 909 (1991); G. Adachi, K. Niki, and J. Shiokawa, J. of Less-Comm. Met., 81, 345 (1981).

This invention proposes to register such expansion, the degree of which is proportional to the amount of hydrogen absorbed, and to measure it by making the deposited $AB_5$ compound an electrode in a capacitive device or a tunneling device, including a MEMS device.

Based on the foregoing, a hydrogen sensor is proposed which has a number of important advantages not available with any other previously known sensor:

(a) the sensor is hydrogen-specific, because only hydrogen penetrates the lattice causing the expansion of the lattice;

(b) the measurement is very quick because the speed of the reactions of hydrogenization and dehydrogenization is extremely high;

(c) carbon monoxide does not poison the sensor if it is maintained at about 115° C.; and (d) oxygen and water do not poison $AB_5$ because the surface of the component A forms a self-limiting oxide/hydroxide layer protecting the sub-surface of the component B and protects the reactivity of the latter towards hydrogen.

See, for example, H. C. Siegmann, L. Schlapbach, and C. R. Brundle, Phys. Rev. Lett., 40, 972 (1978).

A first aspect of the invention provides a device adapted for detecting the presence, and for measuring of, the amount of hydrogen present in an environment, said device comprising a body of a metal hydride hydrogen-absorbent material, said material having a capability to expand upon absorption of said hydrogen, a first electrode, and a dielectric material located between said body of said metal hydride material and said first electrode.

A second aspect of the invention provides a method for detecting the presence, and for measuring, of the amount of hydrogen detected using a sensor, comprising steps of providing a body of a metal hydride hydrogen-absorbent material, said material having a capability to expand upon absorption of said hydrogen, providing a first electrode, providing a dielectric material disposed between said body of said metal hydride material and said electrode, exposing said sensor to an environment which contains or may contain hydrogen, and detecting the presence, and measuring of, the amount of hydrogen contained in said atmosphere using a measuring device capable to measure and register an expansion of said hydrogen-absorbent material upon absorption of said hydrogen.

BRIEF DESCRIPTION OF THE DRAWINGS

The features and advantages of the present invention will be better understood with regard to the following description, appended claims, and accompanying drawings where

DETAILED DESCRIPTION OF THE INVENTION

The sensor of this invention comprises a thin film of a material belonging to an $AB_5$ class of hydrides, wherein the element A is calcium, lanthanum or an element selected from a group consisting of lanthanide rare earth elements (cerium, praseodymium, neodymium, promethium, samarium, europium, gadolinium, terbium, dysprosium, holmium, erbium, thulium, ytterbium, and lutetium), and wherein the element B is an element selected from a group consisting of nickel, cobalt, copper, and platinum. The preferred $AB_5$ hydride is $LaNi_5$. The thin film of an $AB_5$ hydride is present in both embodiments of the sensor discussed below.

The sensor of this invention is built based on the principle that an $AB_5$ hydride lattice expands outwardly when it absorbs hydrogen. This type of sensor is hydrogen-selective because no other gas will be absorbed by an $AB_5$ hydride. The expansion of the $AB_5$ hydride lattice is proportional to the amount of the hydrogen absorbed and can be registered using a capacitance measuring device or a tunnel current measuring device, as subsequently described.

The response of the device to the presence of hydrogen gas can be described as follows. A thin film of preferably $LaNi_5$ lattice, having dimensions of 10 micrometers by 10 micrometers and thickness of 1 micrometer would have a volume of $10^{-10}$ cm$^3$, and having a density of about 5 g/cm$^3$, would weigh about $5 \cdot 10^{-10}$ g. As mentioned above, the gravimetric capacity of $LaNi_5$ (the maximum amount of hydrogen by weight $LaNi_5$ is capable of absorbing) is about 1.5% by weight. Therefore, $7.5 \cdot 10^{-12}$ g of hydrogen can be absorbed by the thin film of $LaNi_5$ described above. Using the Avogadro number, one can compute that $7.5 \cdot 10^{-12}$ g of hydrogen equals to approximately $4.5 \cdot 10^{12}$ atoms of hydrogen. The available surface for hydrogen adsorption, given the dimensions of the thin film of $LaNi_5$ described above, is about $4 \cdot 10^{-7}$ cm$^2$.

The flux of hydrogen to the surface of $LaNi_5$ at an assumed concentration of 1% of hydrogen in air (at 4% hydrogen already forms an explosive mixture with air) is approximately $10^{22}$ molecules/cm$^2 \cdot$sec, and under these conditions the sensor would be exposed to $8 \cdot 10^{15}$ molecules of hydrogen every second of exposure.

Since, as mentioned above, the absorption and subsequent diffusion of hydrogen into the bulk of $LaNi_5$ is extremely quick, the lattice absorbs hydrogen practically instantaneously and expands as a result. The maximum expansion of the lattice is known to be about 8% along a single axis. This expansion is detected and registered by one of the two embodiments of the sensor described below.

Figure 1:
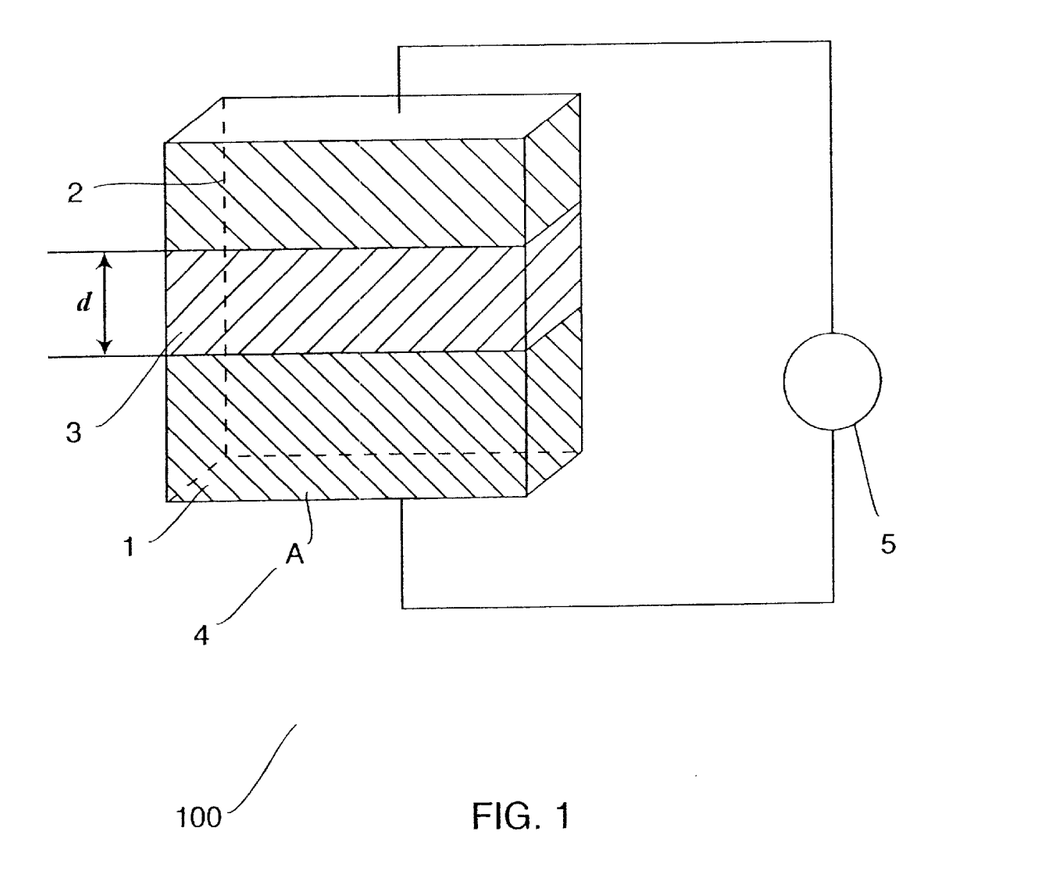
FIG. 1 is a schematic diagram demonstrating the general principle upon which the operation of the sensor of this invention is based and where the detection of hydrogen is accomplished with the use of a capacitive device.
Figure 1A:
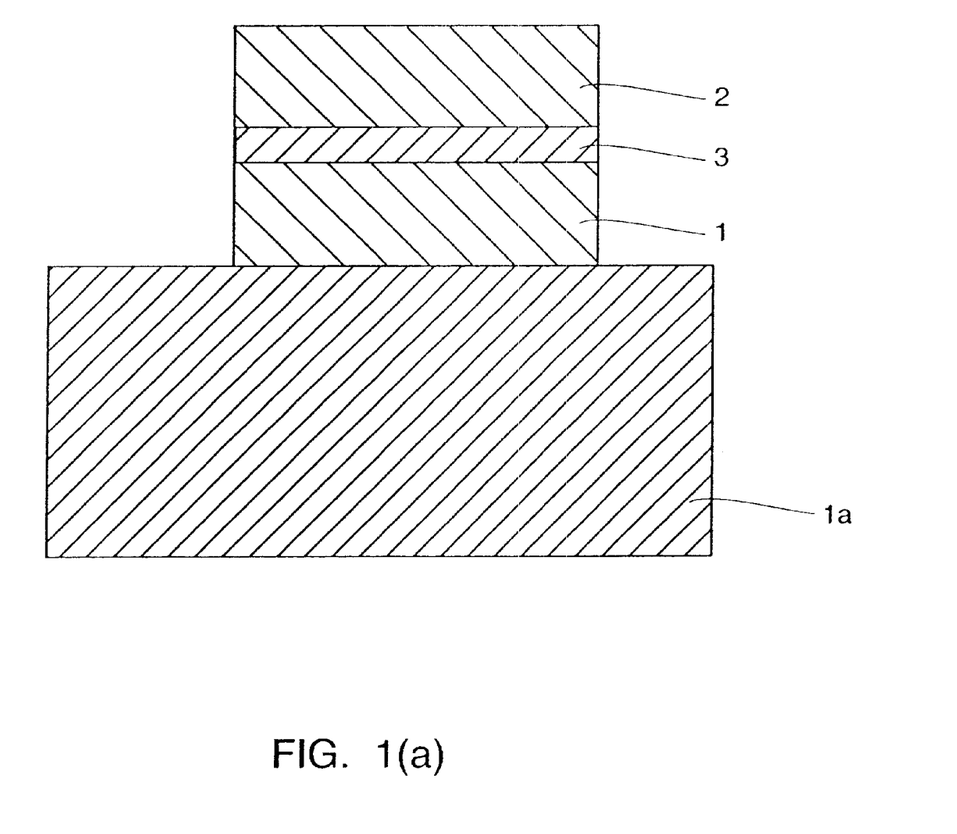
FIG. 1(a) is a schematic diagram showing in more detail relative locations of a substrate, a sensitive film, a dielectric layer and a metal electrode of the sensor generally shown on FIG. 1.

The first embodiment of the sensor is a capacitive device shown schematically in FIGS. 1 and 1(a). The measurement of the expansion of the lattice (caused by the adsorption of hydrogen described above) is conducted as a measurement of the change in capacitance.

The sensor of this first embodiment comprises a thin film 1 of a crystalline material $AB_5$, preferably $LaNi_5$, and a first electrode 2, made of a metal, preferably, gold, separated by a dielectric material 3, preferably, air. The film 1 has a preferred crystallographic orientation such that expansion of a major crystallographic axis of the crystalline material $AB_5$ occurs in a direction perpendicular to the plane of the film 1.

In order to achieve such preferred orientation, the film 1 has a preferred thickness within a range between about 3 micrometers and about 4 micrometers. Alternatively, for epitaxially grown films 1, the thickness of film 1 is between about 0.5 micrometer and about 1 micrometer. The film 1 may have varying lengths and widths as well as varying shapes, but a in preferred embodiment film 1 is a square having dimensions preferably about 10 micrometers by about 10 micrometers and, consequently, a preferred area of about $10^{-4}$ square millimeters.

The film 1 is deposited on a substrate 1a, preferably made of silicon and preferably having thickness of about 50 micrometers, as shown on FIG. 1(a). The film 1 is deposited on the substrate 1a preferably by a method of DC magnetron sputtering. This method is known to those skilled in the art. When the film 1 is a $LaNi_5$ film, separate metal targets of lanthanum, preferably having purity of about 99.9%, and of nickel preferably having purity of about 99.99%, are used. The base pressure of the sputtering system is preferably within the range of low-to-middle $10^{-7}$ Torr.

A compressible material is preferably selected as the dielectric material 3, more preferably, air or a polymeric dielectric, such as teflon (polytetrafluoroethylene), a polyester, or a polyimide. A solid piezoelectric material, such as quartz or lead zirconia titanate (PZT) can also be used as the dielectric material 3.

The non-air dielectric material 3 is deposited directly on top of the film 1, preferably by spin coating for organic dielectric 3, and preferably by the method of vapor phase epitaxy for inorganic dielectric 3. Both methods of spin coating and vapor phase epitaxy are known to those skilled in the art and other methods of depositing the dielectric 3 on top of the film 1 can be used to achieve substantially similar results.

The capacitance of the sensor 100, as shown on FIG. 1, is calculated according to formula (1):

$$C = \in_0 \cdot \in_r \cdot A/d, \quad (1)$$

where C is capacitance, $\in_0$ is permitivity, $\in_r$ is relative dielectric constant, A is the area of adsorption of the device (shown on FIG. 1), and d is thickness of the layer of dielectric 3 (also shown on FIG. 1).

For a given sensor 100, $\in_0$, $\in_r$, and A are all constant. The only variable is thickness d, because when hydrogen 4 is present in the vicinity of the sensor 100, it will be rapidly absorbed by the thin film of $AB_5$ 1, causing the expansion of the thin film of $AB_5$ 1, as described above. This expansion will reduce d, and the capacitance C of sensor 100 will increase. This increase is registered by a capacitance meter 5.

Thickness d of the layer of dielectric 3 and the area A, in case when air is a chosen dielectric material 3, are selected so that the capacitance change of the sensor 100 as a result of hydrogen absorption would be between about 1 pF and about 0.1 aF, preferably between about 1 pF and about 1 aF, these figures of capacitance change being between about 5% and about 10% of the initial capacitance (before the absorption).

The thickness d and the area A are coupled in terms of optimization. Therefore, in case when the film 1 has a mentioned-above preferable area of about $10^{-4}$ square millimeters, and air is used as a preferred dielectric material 3, the thickness d of the dielectric layer 3, is preferably between about 100 Angstroms and about 1000 Angstroms. Such dielectric thickness allows easy detection and measurement of the change in capacitance.

Any device commonly used by those reasonably skilled in the art for measuring capacitance can be used as a capacitance meter 5. If air is used as dielectric, a capacitive bridge circuit known to those reasonably skilled in the art is used for it provides the sensor 100 with the good immunity to noise and drift.

If a material with a higher dielectric constant $\in_r$ is used instead of air, the dimensions of the device can be varied to achieve a higher capacitance range. For such non-air dielectric materials 3, the dielectric thickness d of the layer of dielectric 3 will change somewhat but will remain in a preferred range of between about 100 Angstroms and about 1000 Angstroms.

When air is used as a dielectric material 3, the metal electrode 2 is positioned so that the space d between it and the film 1 be within the range discussed above. In case of non-air dielectric material 3, following depositing such non-air dielectric 3 on top of the film 1, as described above, metal electrode 2 is deposited on top of the dielectric 3, preferably, by a method of vapor deposition, the method being known to those skilled in the art. The thickness of the metal electrode 2 is preferably within a range of between about 1,000 Angstroms and about 2,000 Angstroms for both air and non-air dielectric material 3.

When hydrogen is absorbed, the film 1 will expand upwardly. When air is used as the dielectric 3, and also for non-air dielectrics which are more compliant than the metal of electrode 2, the dielectric will compress. However, there is a possibility that for certain dielectrics 3, both the dielectric 3 and metal electrode 2 will float on top of the film 1, when the film 1 expands. In this case, the device is packaged so that the top of electrode 2 is held mechanically in place.

Figure 1B:
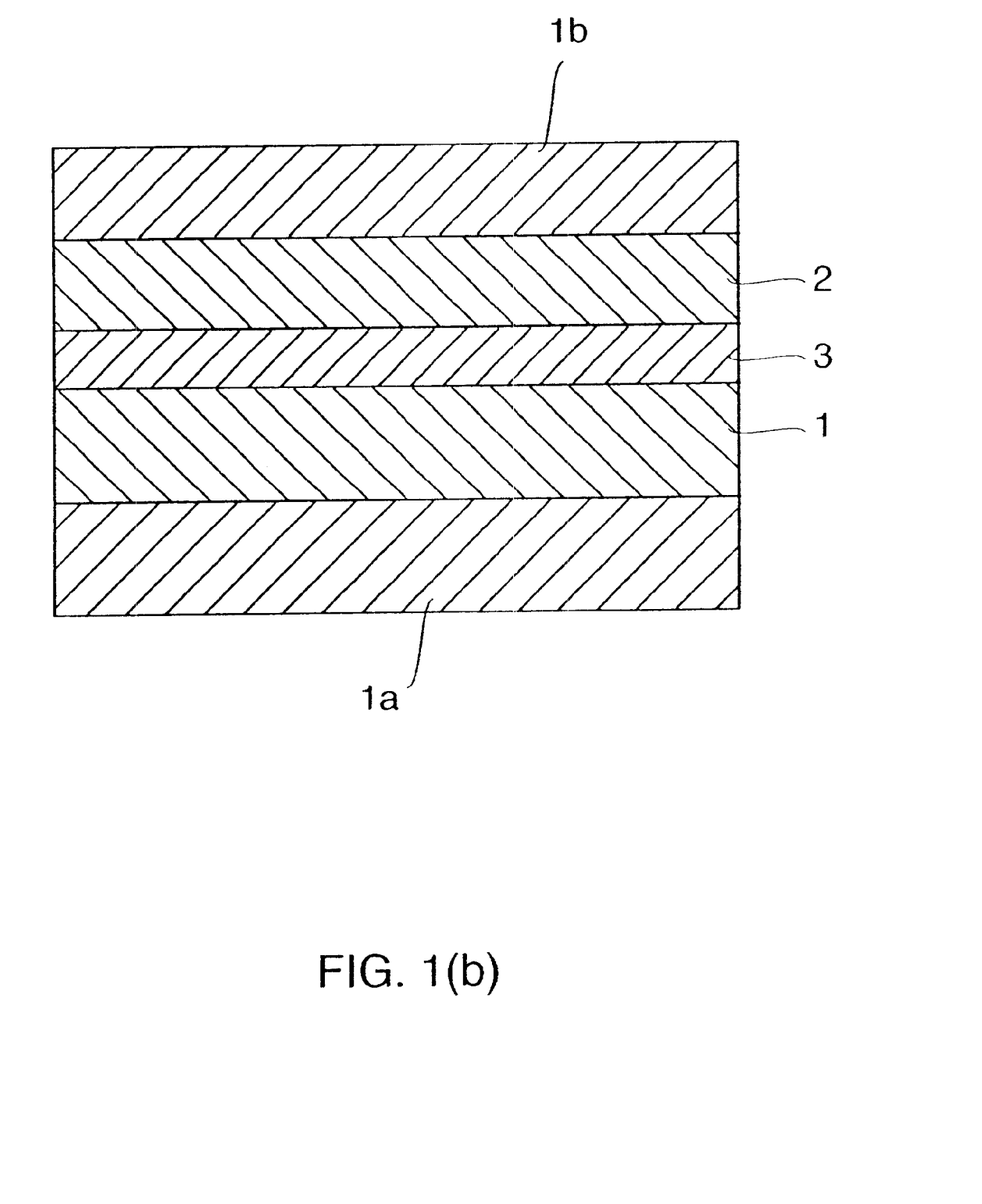
FIG. 1(b) is a schematic diagram showing an embodiment of the sensor based on a capacitive device where the electrode is held in place with the use of mechanical force.

This is accomplished by depositing the metal electrode 2 on a separate, patterned silicon wafer 1b (see FIG. 1(b)) and bonding the two together at the substrate 1a, according to techniques known to those skilled in the art. The entire system is then diced into single sensor units.

The metal of the electrode 2 can be deposited on the patterned silicon wafer 1b to a depth that fills the wells in the pattern of the wafer 1b only partially. In such case, the wafer 1b is partially planarized to remove the top layer of the metal and chemically etched to remove the metal on the side walls, using standard and well known techniques. The two substrates 1a and 1b are then bonded together according to techniques known to those skilled in the art. The entire system is then diced into single sensor units.

When the sensor 100 absorbs hydrogen using the film 1, the film 1 expands and the capacitance change ensues as a result. This change is registered by the capacitance meter 5 as shown on FIG. 1. The sensitivity of the device is such, that the sensor having the LaNi$_5$ film 1 with the dimensions of about 100 micrometers by about 100 micrometers by about 4 micrometers detects an amount of hydrogen creating 7.6 Torr pressure (that is, concentration of hydrogen being about 1% by volume) within about 0.5 seconds.

Figure 2:
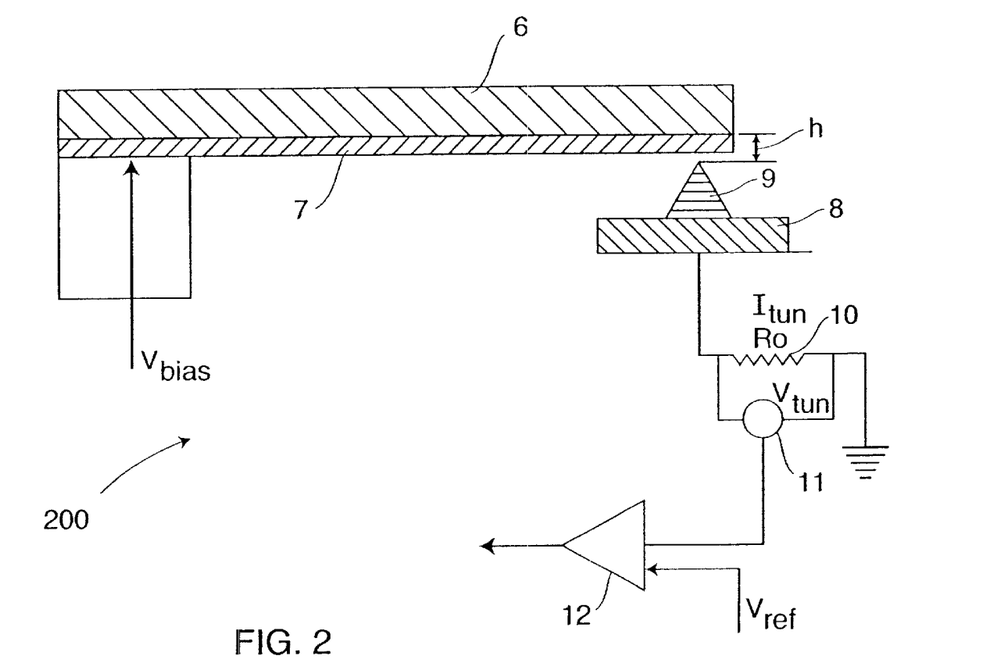
FIG. 2 is a schematic diagram showing a sensor of this invention where the detection of hydrogen is accomplished with the use of a tunneling device.

The second embodiment of the sensor is a tunneling sensor shown schematically in FIG. 2. The measurement of the expansion of the lattice is conducted as a measurement of the tunnel current as follows.

The tunneling sensor 200 is shown schematically on FIG. 2. It comprises a beam 6, preferably made of nickel formed on a thin metal plating base 7, preferably made of gold. A preferred thickness of the beam 6 is about 1 micrometer, the preferred thickness of the metal plating base 7 is about 1000 Angstrom. The plating base 7 is used to generate a surface layer onto which the beam 6 is plated. The plating base is electrically conductive, preferably inert, and forms a base for the electroplating. The beam 6 plays a role of the first electrode.

The beam 6 is positioned in such way that there is a free space having thickness h between the beam 6 and a tip 9 disposed on top of a thin film of AB$_5$ 8, preferably LaNi$_5$. The width of this free space is about 10 Angstroms.

Figure 2A:
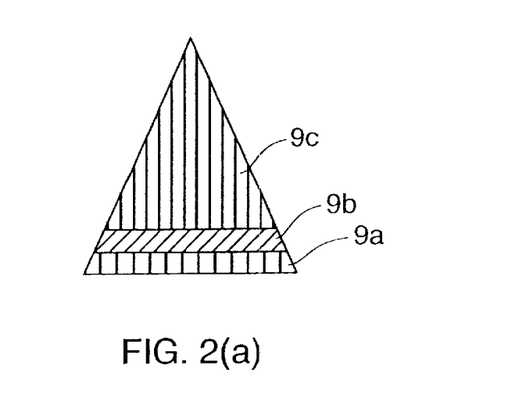
FIG. 2(a) is a schematic diagram showing in more detail a tip of a tunneling device of the sensor generally shown on FIG. 2.

The tip 9 is made of a conductive and, preferably inert, metal and is deposited on top of the film 8 by a method of evaporation using preferably thin layers of titanium 9a and platinum 9b, to insure adhesion, followed by a layer of gold 9c, as shown on FIG. 2(a). The method of evaporation is known to those skilled in the art.

The tip 9 plays a role of a second electrode. The total thickness of the tip 9 is preferably about 1 micrometer and the thickness of layers of titanium 9a and platinum 9b is each within the range of preferably between about 200 Angstroms and 300 Angstroms, the layer of gold 9c having thickness preferably within the range of between about 0.5 micrometers and about 1.5 micrometers.

Voltage $V_{bias}$ is applied to metal plating base 7, generating the tunnel current $I_{tun}$ across a resistor 10 having resistivity $R_0$. The tunnel voltage $V_{tun}$ is measured by a voltmeter 11. Voltage $V_{bias}$ is quite small and is preferably about 0.1 Volt. Excessive voltages could result in heating and other undesirable effects. The tunnel current $I_{tun}$ generated is between about 1 nanoAmpere and about 10 nanoAmperes.

After the thin film 8 absorbed hydrogen, it expands, as described above, moving the tip 9 up and reducing the space h. The tunnel current $I_{tun}$ depends on space h and increases as h decreases with more hydrogen absorbed according to formula (2):

$$I_{tun}=V_{bias}\cdot\exp[-\alpha\cdot\phi^{1/2}\cdot h]/R_0, \qquad (2)$$

wherein $\phi$ is the effective tunneling barrier and is about 0.5 eV (the energy barrier which an electron must surmount to travel from one material to another) and $\alpha$ is a constant.

The tunnel voltage is fed into a comparitor circuit 12. A commonly used comparitor circuit 12 was used, known to those reasonably skilled in the art. The comparitor circuit 12 compares the tunnel voltage and the reference voltage $V_{ref}$ and generates the error signal. The error signal is used to adjust the bias voltage $V_{bias}$ to keep the tunnel current $I_{tun}$ constant. So long as $I_{tun}$ is constant, no ascertainable amount of hydrogen is present. A change of $I_{tun}$ indicates that hydrogen is present. Therefore, by measuring $I_{tun}$, the presence and concentration of hydrogen is detected and measured.

Lattice expansion in this device, on exposure to hydrogen, of the sensor of this embodiment can be inferred in the same way as described above for the embodiment of the sensor using the capacitive device. However, in this device the sensitivity will be an exponential function of the lattice expansion.

Having described the invention in connection with several embodiments thereof, modification will now suggest itself to those skilled in the art. As such, the invention is not to be limited to the described embodiments except as required by the appended claims.

We claim:

1. A device adapted for detecting the presence, and for measuring the amount of hydrogen present in an environment, said device comprising:
    (a) a body of a metal hydride hydrogen-absorbent material, said material having a capability to expand upon absorption of said hydrogen;
    (b) a first electrode; and
    (c) a dielectric material located between said body of said metal hydride material and said first electrode wherein said dielectric material comprises a compressible material.

2. The device of claim 1 further comprising a measuring device capable of measuring and registering an expansion of said hydrogen-absorbent material upon absorption of said hydrogen.

3. The device according to claim 1 or 2, wherein said compressible material is a solid piezoelectric material.

4. The device according to claim 3, wherein said compressible material further comprises air, a polymeric dielectric material, a polyester, and a polyimide.

5. The device according to claim 3, wherein said solid piezoelectric material further comprises quartz and lead zirconia titanate.

6. The device according to claim 1 or 2, further including a second electrode disposed on said body of said metal hydride hydrogen-absorbent material confronting said first electrode, said first electrode and said second electrode defining a space therebetween.

7. The device according to claim 6, wherein said second electrode is made of a material comprising gold.

8. The device according to claim 2, wherein said measuring device comprises a capacitance measuring device and a tunnel current measuring device.

9. The device according to claim 8, wherein said capacitance measuring device detects presence of said hydrogen and measures an amount of said hydrogen by measuring a change in capacitance of said device after said device has been exposed to said hydrogen.

10. The device according to claim 8, wherein said tunnel current measuring device detects presence of said hydrogen and measures an amount of said hydrogen by measuring a change in a tunnel current flowing through said device after said device has been exposed to said hydrogen.

11. The device according to claim 8, wherein said capacitance measuring device further comprises a capacitive bridge circuit.

12. The device according to claim 8, wherein said metal hydride hydrogen-absorbent material has a formula $AB_5$, where A is an element comprising calcium, lanthanum, or an element selected from a group comprising lanthanide rare earth elements, and where B is an element comprising nickel, cobalt, copper, and platinum.

13. The device according to claim 8 or 10, wherein said tunnel current measuring device further comprises:

(a) a beam;

(b) said film of said metal hydride hydrogen-absorbent material with a tip disposed thereupon and facing said beam; and (c) a measuring circuit.

14. The device according to claim 13, wherein said beam is made of a material comprising nickel.

15. The sensor according to claim 13, wherein said measuring circuit further comprises a resistor, a device for measuring said tunnel current and a comparitor unit.

16. The sensor according to claim 13, wherein said tip is made of a material comprising gold.

17. The device according to claim 14, wherein said nickel of which said beam is made is applied on top of a plating base layer, said plating base layer being fabricated of a material comprising gold.

18. The device according to claim 1, wherein said metal hydride hydrogen-absorbent material has a formula $AB_5$, where A is an element comprising calcium, lanthanum, or an element selected from a group comprising lanthanide rare earth elements, and where B is an element comprising nickel, cobalt, copper, and platinum.

19. The device according to claim 1, wherein said first electrode is made of a material comprising gold.

20. A method for detecting the presence, and for measuring, of the amount of hydrogen, using a sensor, said method comprising the steps of:

(a) providing a body of a metal hydride hydrogen-absorbent material, said material having a capability to expand upon absorption of said hydrogen;

(b) providing a first electrode;

(c) providing a dielectric material disposed between said body of said metal hydride material and said electrode wherein said dielectric material comprises a compressible material;

(d) exposing said sensor to an environment which contains or may contain hydrogen; and (e) detecting the presence, and measuring, of the amount of hydrogen contained in said environment using a measuring device capable to measure and register an expansion of said hydrogen-absorbent material upon absorption of said hydrogen.

21. The method according to claim 20, wherein said metal hydride hydrogen-absorbent material has a formula $AB_5$, where A is an element comprising calcium, lanthanum, or an element selected from a group comprising lanthanide rare earth elements, and where B is an element comprising nickel, cobalt, copper, and platinum.

22. The method according to claim 20, wherein said first electrode is made of a material comprising gold.

23. The method according claim 20, wherein said compressible material and is a solid piezoelectric material.

24. The method according to claim 23, wherein said compressible material further comprises air, a polymeric dielectric material, a polyester, and a polyimide.

25. The method according to claim 23, wherein said solid piezoelectric material further comprises quartz and lead zirconia titanate.

26. The method according to claim 20, wherein said measuring device comprises a capacitance measuring device and a tunnel current measuring device.

27. The method according to claim 26, wherein said capacitance measuring device detects presence of said hydrogen and measures an amount of said hydrogen by measuring a change in capacitance of said sensor after said sensor has been exposed to said hydrogen.

28. The method according to claim 26, wherein said tunnel current measuring device detects presence of said hydrogen and measures an amount of said hydrogen by measuring a change in a tunnel current flowing through said sensor after said sensor has been exposed to said hydrogen.

29. The method according to claim 26, wherein said capacitance measuring device further comprises a capacitive bridge circuit.

30. The method according to claim 26, wherein said tunnel current measuring device further comprises:

(a) a beam;

(b) said body of said metal hydride hydrogen-absorbent material with a tip disposed thereupon; and (c) a measuring circuit.

31. The method according to claim 30, wherein said beam is made of a material comprising nickel.

32. The method according to claim 31, wherein said metal hydride hydrogen-absorbent material has a formula $AB_5$, where A is an element comprising calcium, lanthanum, or an element selected from a group comprising lanthanide rare earth elements, and where B is an element comprising nickel, cobalt, copper, and platinum.

33. The method according to claim 31, wherein said nickel of which said beam is made is applied on top of a plating base layer, said plating base layer being fabricated of a material comprising gold.

34. The method according to claim 30, wherein said tip is made of a material comprising gold.

35. The method according to claim 30, wherein said measuring circuit further comprises a resistor, a device for measuring said tunnel current and a comparitor unit.

36. The method according to claim 20, wherein said sensor further includes a second electrode disposed on said body of said metal hydride hydrogen-absorbent material confronting said first electrode, said first electrode and said second electrode defining a space therebetween.

37. The method according claim 36, wherein said second electrode is made of a material comprising gold.

* * * * *